United States Patent
McLeod et al.

(10) Patent No.: US 11,000,202 B2
(45) Date of Patent: May 11, 2021

(54) SYSTEMS AND METHODS FOR MAPPING AND MODULATING REPOLARIZATION

(71) Applicant: Mayo Foundation for Medical Education and Research, Rochester, MN (US)

(72) Inventors: Christopher J. McLeod, Rochester, MN (US); Samuel J. Asirvatham, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 16/805,094

(22) Filed: Feb. 28, 2020

(65) Prior Publication Data

US 2020/0196893 A1    Jun. 25, 2020

Related U.S. Application Data

(63) Continuation of application No. PCT/US2019/016644, filed on Feb. 5, 2019.

(60) Provisional application No. 62/626,448, filed on Feb. 5, 2018.

(51) Int. Cl.
| | | |
|---|---|---|
| *A61B 5/04* | (2006.01) | |
| *A61B 5/0245* | (2006.01) | |
| *A61B 5/042* | (2006.01) | |
| *A61B 5/046* | (2006.01) | |
| *A61B 5/00* | (2006.01) | |

(52) U.S. Cl.
CPC ........ *A61B 5/04014* (2013.01); *A61B 5/0245* (2013.01); *A61B 5/046* (2013.01); *A61B 5/0422* (2013.01); *A61B 5/6858* (2013.01); *A61B 5/7203* (2013.01); *A61B 5/725* (2013.01)

(58) Field of Classification Search
CPC ... A61B 5/04014; A61B 5/725; A61B 5/0245; A61B 5/0422; A61B 5/7203; A61B 5/6858; A61B 5/046
See application file for complete search history.

(56) References Cited

U.S. PATENT DOCUMENTS

| | | |
|---|---|---|
| 5,813,991 A | 9/1998 | Willis et al. |
| 8,078,272 B2 | 12/2011 | Lin |
| 2014/0052119 A1* | 2/2014 | Stewart .................. A61B 5/042 606/33 |
| 2016/0183810 A1 | 6/2016 | Laughner et al. |
| 2018/0368714 A1* | 12/2018 | Gutbrod ............... A61B 5/6858 |
| 2019/0246930 A1* | 8/2019 | Zhu ...................... A61B 5/6859 |

OTHER PUBLICATIONS

International Search Report & Written Opinion in International Application No. PCT/US2019/016644 dated Apr. 30, 2019, 14 pages.
International Preliminary Report on Patentability directed to related International Patent Application No. PCT/US2019/016644, dated Aug. 11, 2020; 7 pages.

* cited by examiner

*Primary Examiner* — Rex R Holmes
(74) *Attorney, Agent, or Firm* — Sterne, Kessler, Goldstein & Fox P.L.L.C.

(57) ABSTRACT

This document describes methods and materials for mapping and modulating repolarization. For example, this document relates to methods and devices for mapping and modulating repolarization to target atrial and ventricular arrhythmias to deliver electrical stimulation pacing, ablation and/or electroporation.

15 Claims, 2 Drawing Sheets

SYSTEMS AND METHODS FOR MAPPING AND MODULATING REPOLARIZATION

CROSS-REFERENCE TO RELATED APPLICATIONS

This application is a Continuation under 35 U.S.C. § 111(a) of International Application No. PCT/US2019/016644, filed on Feb. 5, 2019, which claims the benefit of U.S. Provisional Application Ser. No. 62/626,448, filed on Feb. 5, 2018. The disclosures of the prior applications are considered part of the disclosure of this application and are incorporated in their entirety into this application.

BACKGROUND

1. Technical Field

This document relates to methods and materials for mapping and modulating repolarization. For example, this document relates to methods and devices for mapping and modulating repolarization to target atrial and ventricular arrhythmias to deliver electrical stimulation pacing, ablation, and/or electroporation.

2. Background Information

Abnormalities in cardiac repolarization, such as temporal fluctuations and aberrations in spatial heterogeneity, promote an abnormal electrophysiological substrate which is intrinsically linked to the genesis of cardiac arrhythmias, particularly sudden cardiac death arrhythmias, ventricular fibrillation, and polymorphic ventricular tachycardia. Current cardiac mapping techniques, such as acquiring local electrograms, detect abnormalities focusing on the cardiac activation sequence and depolarization, which can be a minimal contributor to these sudden death arrhythmias.

More than half of fatal cardiac arrhythmias involve abnormalities in repolarization, for example, Tosades de Pointes, triggered ventricular fibrillation, early after depolarizations, and the various arrhythmias seen in congenital and acquired long QT syndrome. Electrical activation can be mapped and displayed. The electrical activation can be displayed and registered as a three-dimensional electroanatomic construct to enable more effective recording of ablation for arrhythmia management. The mapping can aid the physician in identifying and diagnosing abnormalities, based on cardiac depolarization. Multiple methods for cardiac mapping, as well as ablation, modulation, and pacing techniques, have been developed for cardiac depolarization.

Depolarization maps can be used to find the source of various atrial and ventricular arrhythmias and modulate depolarization with pacing, ablation, and other energy deliveries including electroporation. A monophasic action potential (MAP) can be recorded ex-vivo. Drugs and ablation techniques focus on depolarization, however, they can worsen the propensity for arrhythmia by creating a more arrhythmogenic repolarization profile, which can be unrecognizable to an electrophysiologist. However, many arrhythmias, both inherited and acquired, are reliant or triggered on abnormal cardiac repolarization.

SUMMARY

This document describes methods and materials for mapping and modulating repolarization. For example, this document relates to methods and devices for mapping and modulating repolarization to target atrial and ventricular arrhythmias to deliver electrical stimulation pacing, ablation, and/or electroporation.

In one aspect, this disclosure is directed to a method of treating cardiac arrhythmias. The method can include receiving a repolarization signal from a first electrode. The electrode can be located on a distal portion of a mapping catheter while the distal portion of the mapping catheter is inserted in a heart of a patient such that the first electrode is located at a first location. The method can include filtering the repolarization signal received from the first electrode, delivering stimulation to the heart via the first electrode, and creating a repolarization map of the heart. In some cases, filtering the repolarization signal can include reducing noise from the repolarization signal. In some cases, filtering the repolarization signal can include calculating a differential of the repolarization signal, and removing the derivative signal from the repolarization signal.

In some cases, the method can include receiving an external signal from a second electrode external to the heart at a second location, and calibrating the external signal with the repolarization signal from the first electrode. In some cases, the first location and the second location can receive signals from a similar area of the heart. In some cases, calibrating the external signal can include moving the external electrode to a third location, and creating the repolarization map of the heart can include using the external signal to create the repolarization map. In some cases, calibrating the external signal can include taking a first order differential of the external signal. In some cases, calibrating the external signal can include measuring a downslope of the t-wave intersection with a baseline.

In some cases, the method can include delivering electroporation to the heart via the first electrode. In some cases, the method can include delivering electroporation comprises delivering irreversible electroporation. In some cases, delivering electroporation can include delivering reversible electroporation. In some cases, the method can include receiving an electroporation signal caused by delivering electroporation and detecting a predictable effect of electroporation on the repolarization signal.

In some cases, delivering stimulation can include delivering a first set of stimulation below a threshold. In some cases, delivering stimulation can include increasing a parameter of the first set of stimulation. In some cases, delivering stimulation can include detecting capture is obtained. In some cases, delivering stimulation can include decreasing an intensity of the first set of stimulation and changing an interval between pulses of the first set of stimulation. In some cases, delivering stimulation can include changing a heart rate of the patient via the stimulation. In some cases, changing the heart rate of the patient causes a change in the repolarization signal of the patient.

In some cases, creating the repolarization map can include creating the repolarization with magnet-aided navigation and point procurement. In some cases, creating the repolarization map can include determining a reference point in the repolarization signal. In some cases, creating the repolarization map can include using the reference point to create the repolarization map. In some cases, the reference point can be an end of repolarization. In some cases, the method can include determining variants of the repolarization map from a normal repolarization map. In some cases, determining variants of the repolarization map can include comparing the repolarization map with the normal repolarization map and detecting differences between the repolarization map and the normal repolarization map.

In another aspect, this disclosure is directed to a system for treating cardiac arrhythmias. The system can include a first electrode, a memory that is capable of storing computer executable instructions, and a processor that is configured to facilitate execution of the executable instructions stored in memory. The instructions can cause the processor to receive a repolarization signal from a first electrode located at a first location, filter the repolarization signal receiving from the electrode, deliver stimulation to the heart via the electrode, and create a repolarization map of the heart. In some cases, filtering the repolarization signal can include reducing noise from the repolarization signal. In some cases, filtering the repolarization signal can include calculating a differential of the repolarization signal, and removing the derivative signal from the repolarization signal. In some cases, the instructions can cause the processor to receive an external signal from a second electrode external to the heart at a second location, and calibrate the external signal with the repolarization signal from the first electrode. In some cases, the first location and the second location can receive signals from a similar area of the heart.

In some cases, creating the repolarization map of the heart can include using the external signal to create the repolarization map. In some cases, calibrating the external signal can include taking a first order differential of the external signal. In some cases, calibrating the external signal can include measuring a downslope of the t-wave intersection with a baseline. In some cases, the instructions can cause the processor to deliver electroporation to the heart via the first electrode. In some cases, delivering electroporation can include delivering irreversible electroporation. In some cases, delivering electroporation can include delivering reversible electroporation.

In some cases, the instructions can cause the processor to receive an electroporation signal caused by delivering electroporation and detect a predictable effect of electroporation on the repolarization signal. In some cases, delivering stimulation can include delivering a first set of stimulation below a threshold. In some cases, delivering stimulation can include increasing a parameter of the first set of stimulation. In some cases, delivering stimulation can include detecting capture is obtained. In some cases, delivering stimulation can include decreasing an intensity of the first set of stimulation and changing an interval between pulses of the first set of stimulation.

In some cases, delivering stimulation can include changing a heart rate of the patient via the stimulation. In some cases, changing the heart rate of the patient causes a change in the repolarization signal of the patient. In some cases, creating the repolarization map can include creating the repolarization with magnet-aided navigation and point procurement. In some cases, creating the repolarization map can include determining a reference point in the repolarization signal. In some cases, creating the repolarization map can include using the reference point to create the repolarization map. In some cases, the reference point is an end of repolarization. In some cases, the instructions can cause the processor to determine variants of the repolarization map from a normal repolarization map. In some cases, determining variants of the repolarization map can include comparing the repolarization map with the normal repolarization map and detecting differences between the repolarization map and the normal repolarization map.

Particular embodiments of the subject matter described in this document can be implemented to realize one or more of the following advantages. The devices and methods can better characterize electrical properties of the heart, such as for the treatment of cardiac arrhythmia. In addition, mapping abnormal and normal cardiac repolarization can increase understanding, risk stratification, and treatment of cardiac arrhythmias, such as polymorphic ventricular tachycardia and ventricular fibrillation. The devices and methods can be used for mapping of both ventricular tissue and atrial tissue. Further, the devices and methods can receive data on monophasic action potentials, providing information regarding cardiac repolarization. The devices and methods can provide pressure sensors in the tip of the catheter such that proximal electrodes can remain in the blood pool and excessive catheter tip pressure does not distort the cellular milieu and associated repolarization characteristics. Further, the devices and methods can simultaneously detect cardiac repolarization abnormalities and provide treatment energy. Also, the devices and methods can reduce time and labor burdens, while increasing spatial resolution.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description, drawings, and from the claims.

DESCRIPTION OF DRAWINGS

Like reference numbers represent corresponding parts throughout.

DETAILED DESCRIPTION

This document describes methods and materials for mapping and modulating repolarization. For example, this document relates to methods and devices for mapping and modulating repolarization to target atrial and ventricular arrhythmias to deliver electrical stimulation pacing, ablation, and/or electroporation.

Abnormalities in cardiac repolarization, such as temporal fluctuations and aberrations in spatial heterogeneity, promote an abnormal electrophysiological substrate which is intrinsically linked to the genesis of cardiac arrhythmias, particularly sudden cardiac death arrhythmias, ventricular fibrillation, and polymorphic ventricular tachycardia. More than half of fatal cardiac arrhythmias involve abnormalities in repolarization, for example, Tosades de Pointes, triggered ventricular fibrillation, early after depolarizations, and the various arrhythmias seen in congenital and acquired long QT syndrome. While depolarization is a discrete event, which can be easy to map due to the distinct start and end points, repolarization is gradual, which can be more difficult to map. Repolarization can also occur over a longer period of time, making start and stop times more difficult to determine. In addition, a frequency and/or amplitude of repolarization can be similar to electrical noise. Accordingly, filtering out background noise from a repolarization signal can be problematic.

The devices and methods provided herein can better characterize electrical properties of the heart, such as for the treatment of cardiac arrhythmia. In addition, the devices and methods can collect data on monophasic action potentials, providing information regarding cardiac repolarization. Further, the devices and methods can simultaneously detect cardiac repolarization abnormalities and provide treatment energy. The devices and methods can provide feedback electroporation and stimulation based modulation so as to measure and optimize repolarization times to prevent malignant cardiac arrhythmias.

Figure 1:
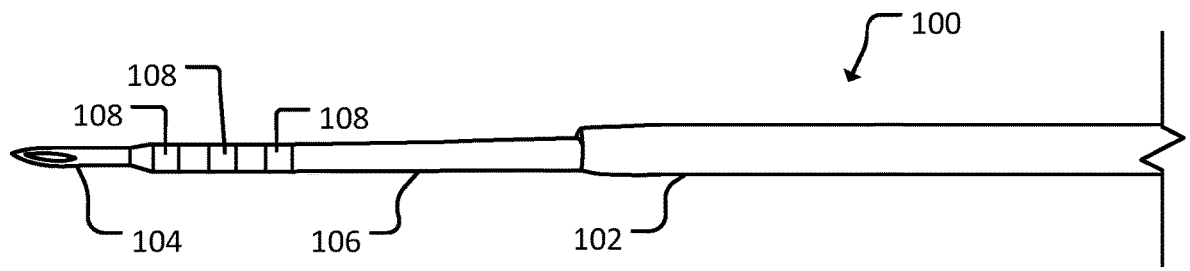
FIG. 1 is a schematic of a mapping catheter, in accordance with some embodiments provided herein.

Referring to FIG. 1, a mapping catheter 100 is shown. Mapping catheter 100 can include a catheter sheath 102 and a probe 106. In some cases, probe 106 can include a tip portion 104. In some cases, probe 106 can include one or more electrodes 108.

Catheter sheath 102 can be used to navigate mapping catheter 100 into a heart of a patient. Accordingly, catheter sheath 102 can have adequate maneuverability. In some cases, the catheter can be used for placement external to the heart. In some cases, catheter sheath 102 can be inserted to the heart via percutaneous venous or arterial access. In some cases, the mapping catheter 100, or components thereof, can be coupled to an external monitoring system. In some cases, the external monitoring system can provide filtering, signal processing, monitoring, catheter location, and ablation capabilities. In some cases, the external monitoring system can include a pulse generator to produce DC and/or AC stimulation pulses. In some cases, catheter sheath 102 and/or probe 106 can include an internal lumen. In some cases, the internal lumen can provide suction and/or irrigation. In some cases, irrigation can be used for improving ablation. In some cases, internal lumen can be associated with less thrombus and/or coagulation in and around a site of ablation.

Tip portion 104 can be plunged into a portion of the heart. In some cases, tip portion 104 can be an electrode. In some cases, tip portion 104 can include an electrode. In some cases, tip portion 104 can include a plurality of electrodes. Optionally, tip portion 104 can be a blunt atraumatic tip that would come into contact with a myocardium but does not cause penetration of the myocardium. In some cases, one or more electrodes can be located on or near tip portion 104. In some cases, tip portion 104 can be a single spoke, a tine, a hook, a helix, or other component capable of piercing tissue. In some cases, tip portion 104 can include an opening providing access to the lumen of the probe 106 and/or catheter sheath 102. In some cases, tip portion 104 can be registered using impedance based monitoring or electromagnetic field location. In some cases, impedance based monitoring or electromagnetic field location can be used to determine a location and/or an orientation of mapping catheter 100.

In some cases, electrodes 108 can be located on a free end of the probe (e.g., near tip portion 104). Electrodes 108 can be linearly spaced along probe 106. In some cases, electrodes 108 can be used for data collection. In some cases, electrodes 108 can be used to provide stimulation. In some cases, electrodes 108 can be unipolar, bipolar, multipolar, etc. In some cases, electrodes 108 can be spaced in such a way that enough separation is provided for a reference potential and that tip portion 104 of the probe 106 will be in contact with an endocardial or epicardial surface of the heart. In some cases, the electrodes 108 can be spaced apart from tip portion 104 such that tip portion 104 can pierce tissue, while electrodes 108 remain outside the tissue.

In some cases, electrodes 108 can record a monophasic action potential of the heart, or other tissue. In some cases, electrodes 108 can record unipolar and/or bipolar electrograms. In some cases, electrodes 108 can record simple electrical activity (e.g., cardiac depolarization). In some cases, electrodes 108 can provide stimulation (e.g., electroporation, ablation, etc.). In some cases, electrodes 108 can be connected, via leads, to a multichannel central terminal for filtering, signal processing, and/or interpretation. In some cases, conductors can be used to transmit signals from electrodes 108 to a central processing terminal. In some cases, the signals, or processed signals, can be displayed on a user interface. In some cases, the signals, or processed signals, can be displayed for live interpretation. In some cases, the location of the mapping catheter 100 and the signals can be combined into an image. In some cases, the image can show cardiac activation, and/or repolarization characteristics. In some cases, the image can be derived from the monophasic action potential recordings.

In some cases, mapping catheter 100 can map cardiac depolarization, cardiac repolarization, and/or provide a stable reference for pressure sensing. In some cases, constant, or substantially constant, pressure, can be used to prevent or limit injury to the cells of the heart. In addition, constant, or substantially constant, pressure can maintain a stable action potential reflection. In some cases, mapping catheter 100 can include a pressure sensing component and/or a force sensing component. In some cases, the pressure and/or force sensing component can be located in tip portion 104. In some cases, the pressure and/or force sensing component can be a resilient element coupled between a distal tip (e.g., tip portion 104) and a proximal portion of the mapping catheter 100.

Figure 2:
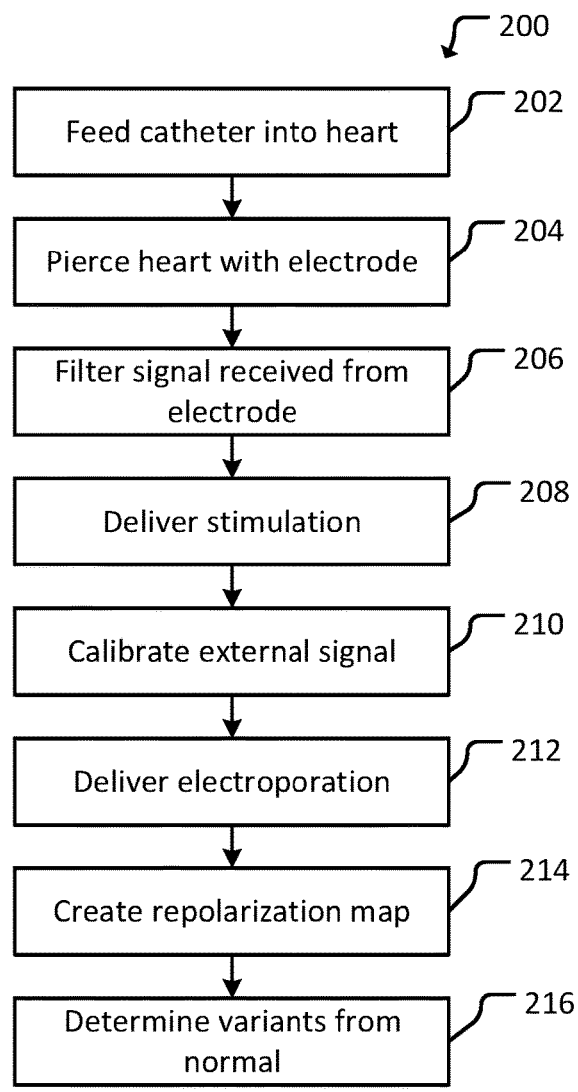
FIG. 2 is a method of measuring and optimizing repolarization times to treat cardiac arrhythmias, in accordance with some embodiments provided herein.

Referring to FIG. 2, a method 200 of measuring and optimizing repolarization times to treat cardiac arrhythmias is shown. Method 200 can include feeding a catheter into a heart at 202, piercing the heart with an electrode at 204, filtering a signal received from the electrode at 206, delivering stimulation at 208, calibrating an external signal at 210, delivering electroporation at 212, creating a repolarization map at 214, and determining variants from normal at 216.

Feeding a catheter into a heart at 202 can include positioning a catheter into the heart. In some cases, the catheter can be mapping catheter 100. In some cases, the catheter can include an external monitoring system. The external monitoring system can be capable of recording with variable sampling rates. In some cases, the sampling rate can be high (e.g., greater than 5000 Hz). In some cases, the external monitoring system can also include a variable dynamic range for timed recording of repolarization. In some cases, the dynamic range can be large (e.g., 2-20 dB, 100-200 dB, or greater). In some cases, the catheter can be capable of recording simultaneous repolarization signals to provide spatial resolution. In some cases, the catheter can record depolarization and repolarization as a single signal.

Piercing the heart with an electrode at 204 can include piercing the heart with a tip portion 104 of mapping catheter 100. Piercing the heart with an electrode at 204 can include obtaining a recording from the electrode. In some cases, piercing the heart can cause a disruption of cells of the heart, which can be recorded with the electrode. In some cases, piercing the heart can cause disruption of a repolarization of the cell, which can be recorded with the electrode. In some cases, piercing the heart can cause a repolarization artifact that is different from an actual repolarization signal. In some cases, a repolarization signal that is undisturbed has a duration which is different from a duration of the disrupted repolarization signal. In some cases, this difference in duration can be predictable, such that the repolarization signal can be reflective of the normal signal and a signal caused by the plunge of the electrode, which can be broken down into distinct portions. In some cases, the repolarization signal caused by the plunge electrode can be an abrupt repolarization.

Filtering a signal received from the electrode at 206 can include reducing and/or removing noise from the signal. In some cases, filtering can aid in enhancing detection of repolarization changes. In some cases, filtering can enable separation of vital cardiac structures (e.g., Purkinje, epicardial and supravalvular structures) electrical signals. In some cases, the vital cardiac structures electrical signals can be separated individually or from a normal endocardium. In some cases, filtering a signal can include calculating a differential of the signal (e.g., an electrogram) received from the electrodes on mapping catheter 100. In some cases, a differential can be calculated on multiple electrograms. In some cases, electrodes can be located on multiple sides of the myocardium, and each signal can be separately filtered. For example, a differential can be calculated on electrograms tested both at wide and narrow filter settings. Filtering the signal can distinguish between myocardial injury caused by the piercing of the heart at 204, and the electrogram showing repolarization interval. In some cases, the signal can be simultaneously filtered while the derivative is being taken such that the derivative signal is filtered out, removing the plunge electrode artifact and obtaining the repolarization signal. In some cases, high frequency components can be filtered out. In some cases, high frequency components can be filtered out when the derivate of the signal is taken.

Delivering stimulation at 208 can include delivering a set of stimulation pulses. In some cases, delivering stimulation at 208 can include delivering stimulation via electrodes 108 on mapping catheter 100. In some cases, delivering stimulation can be done simultaneously with recording. In some cases, stimulation can be delivered on a first subset of electrodes 108 and signals can be recorded on a second subset of electrodes 108. Delivering stimulation at 208 is described in greater detail with respect to FIG. 3.

Calibrating an external signal at 210 can be done after establishing a repolarization time. In some cases, an external signal can include recordings from external recording systems, intracardial electrodes, pericardial electrodes, or other electrodes. In some cases, calibrating an external signal can include gathering recordings from external systems that are in a similar location as the plunge electrode. In some cases, once the area of the plunge electrode is mapped, a surface electrode can be moved to generate a map of the entire heart. In some cases, calibrating an external signal can include taking a first order differential of the signal. In some cases, calibrating an external signal can include measuring a downslope of the t-wave intersection with a baseline. In some cases, calibrating an external signal can be used to validate noninvasive recording and/or other intracardiac recordings. In some cases, calibrating an external signal can aid in limiting the number of locations for deploying a plunge electrode. In some cases, once the plunge electrode and surface electrode (or other electrodes) are calibrated, the surface electrode can be moved and used to determine the mapping of the heart, without moving the plunge electrode.

Delivering electroporation at 212 can include delivering electrical field pulses across cells. In some cases, the electrical field pulses can include short (e.g., microsecond) pulses. In some cases, electrical field pulses can include high intensity pulses. In some cases, electroporation can be delivered such that irreversible defects (pores) occur in the cell membrane lipid layer. In some cases, irreversible electroporation can cause a loss of cell homeostasis, resulting in cell death from apoptosis. By delivering irreversible electroporation with electrical stimulation, non-cellular tissue structure can be unaffected, limiting significant damage to heart tissue surrounding the location of electroporation. In some cases, delivering electroporation can include delivering reversible electroporation. In some cases, reversible electroporation can change transmembrane currents so as to affect repolarization and depolarization intervals. In some cases, reversible electroporation can cause predictable effects in repolarization and depolarization. In some cases, hyperpolarization can be caused by electroporation at varying coupling intervals. Accordingly, as further titration of the reversible electroporation is delivered, a predictable effect on repolarization can be detected until irreversible electroporation doses are achieved. In some cases, electroporation can be delivered with a low voltage (e.g., 10 to 2000 mV) and a long pulse duration (e.g., 0.5 to 1 seconds). In some cases, electroporation can be delivered with a high voltage (e.g., 10 to 50 V) and a short pulse duration (e.g., 0.001 msec).

Creating a repolarization map at 214 can include creating a single repolarization map, or a plurality of repolarization maps. In some cases, creating a repolarization map can include creating a three-dimensional map image. In some cases, three dimensional maps can be created with magnet-aided navigation and point procurement. In some cases, the three-dimensional transmural repolarization map can be superimposed with a simultaneously acquired depolarization map(s). In some cases, the three-dimensional transmural repolarization map can be separately displayed from a simultaneously acquired depolarization map(s).

Determining variants from normal at 216 can include using the repolarization maps, and/or the depolarization maps, to determine points of pathology and variants from a normal. In some cases, the three-dimensional repolarization maps can be compared with a template of normal and/or desired timings for a depolarization sequence. In some cases, after determining points of pathology and/or variants from normal, electroporation can be delivered to sites of pathology (e.g., as described with respect to step 212). In some cases, electroporation can be titrated in real time with the recorded repolarization times. In some cases, electroporation can be titrated such that the energy delivered can be increased to irreversible doses. In some cases, electroporation can be stopped before reaching irreversible doses if a beneficial effect has occurred. In some cases, a beneficial effect can include changes toward a normal pattern as detected via comparison with the template maps.

In some cases, method 300 can also include changing a heart rate. In some cases, changing a heart rate can include providing stimulation to the heart to modify the heart rate. In some cases, changing a heart rate can change a repolarization signal. In some cases, by changing a heart rate, a pattern created by the plunge electrode can be saturated. In some cases, the heart rate can be changed and the repolarization can be mapped for a plurality of heart rates. In some cases, if repolarization shows similar activity in the plurality of repolarization maps, it can be determined that the maps indeed show repolarization. In some cases, if the repolarization does not show similar activity in the plurality of repolarization maps, a new repolarization reference point may be selected to create the repolarization maps.

Figure 3:
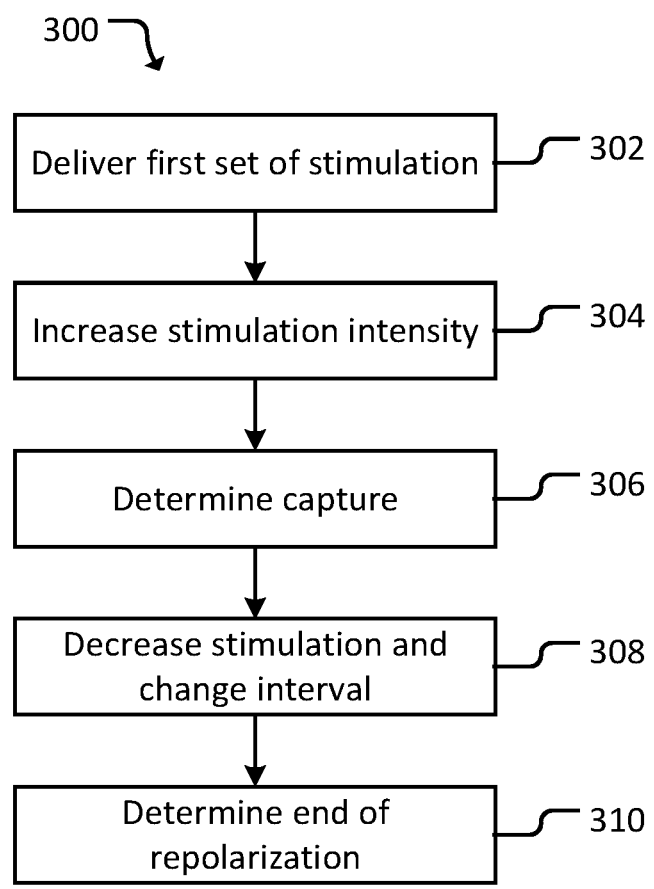
FIG. 3 is a method of providing stimulation and determining an end of repolarization, in accordance with some embodiments provided herein.

Referring to FIG. 3, a method 300 of providing stimulation and determining an end of repolarization is shown. Method 300 can include delivering a first set of stimulation at 302, increasing stimulation intensity at 304, determining a capture at 306, decreasing stimulation and changing a stimulation interval at 308, and determining an end of repolarization at 310. In some cases, part or all of method 300 can be used for delivering stimulation at 208 of method 200.

Delivering a first set of stimulation at 302 can include delivering a subthreshold stimulation. In some cases, the first set of stimulation has an amplitude below a threshold. In some cases, the first set of stimulation has an intensity below a threshold. In some cases, the first set of stimulation can include stimulation pulses. In some cases, the first set of stimulation can be delivered via a first set of electrodes, while the resulting signal can be received from a second set of electrodes. In some cases, the subthreshold stimulation can cause a small after potential (e.g., in a monophasic signal). In some cases, an after potential can be caused by the stimulation when a refractory phase of the heart is over. In some cases, the subthreshold stimulation can produce an after potential when the repolarization time has expired.

Increasing stimulation intensity at 304 can include increasing a parameter of the stimulation. In some cases, increasing stimulation intensity can include increasing an amplitude of the stimulation. In some cases, increasing stimulation intensity can include increasing the intensity of the stimulation until a threshold is crossed. In some cases, the stimulation intensity can be increased until capture is obtained. In some cases, capture can be used to determine if the plunge electrode is in a location adequate for determining an end of repolarization. In some cases, the suprathreshold stimulation can produce a second action potential, but the second action potential will not be produced within a true refractory period.

Determining a capture at 306 can include determining a capture is obtained when the stimulation intensity crosses a threshold. Optionally, determining a capture can include determining when a signal in response to the stimulation crosses a threshold. In some cases, steps 302-306 can be repeated at various depths of the myocardium. In some cases, steps 302-306 can be repeated at various heights of the myocardium.

Decreasing stimulation and changing a stimulation interval at 308 can include decreasing a stimulation intensity of the stimulation. In some cases, decreasing a stimulation intensity can include decreasing an amplitude of stimulation. In some cases, changing a stimulation interval can include decreasing a time interval between stimulation pulses. In some cases, changing a stimulation interval can include modifying the time interval between stimulation pulses until no after potential is detected. In some cases, by modifying the time interval and checking for an after potential, or lack thereof, the system can confirm that the repolarization signal was not filtered out of the signal.

Determining an end of repolarization at 310 can include determining an end of repolarization when no after potential is detected. In some cases, determining an end of repolarization can be used as a reference to create a repolarization map. In some cases, other reference points may be detected. For example, a beginning, middle, or other reference point may be used as a reference point for repolarization. In some cases, the repolarization map(s) can be based on the other reference points. In some cases, various reference points can be determined and compared to determine which to reference point, or points, are more relevant for creating a repolarization map. After the end of repolarization is determined at 310, or another reference point is determined, the signal can be calibrated, as described in step 210 of method 200, as described with respect to FIG. 2.

In some cases, methods 200 and 300 can be used with other electrode configurations. In some cases, the electrode configuration can include a multielectrode basket. In some cases, the multielectrode basket can be deployed in a pericardial space or within the heart. In some cases, the multielectrode basket can include a nanoscale electrode. In some cases, the multielectrode basket can include a tensing and/or conducting graphene or graphene-like material. In some cases, electrodes used for performing methods 200 and/or 300 can be located in extracardiac structures. In some cases, extracardiac structures can include the gastrointestinal tract, the bronchial smooth muscle, skin electrical activity, peripheral autonomic, and central nervous systems neural and brain activity, etc.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the process depicted in the accompanying figures do not necessarily require the particular order shown, or sequential order, to achieve desirable results. In certain implementations, multitasking and parallel processing may be advantageous.

What is claimed is:

1. A method of treating cardiac arrhythmias, the method comprising:
  receiving a repolarization signal from a first electrode on
    a distal portion of a mapping catheter while the distal portion of the mapping catheter is inserted in a heart of a patient such that the first electrode is located at a first location;

filtering the repolarization signal received from the first electrode;

delivering stimulation to the heart via the first electrode;

creating a repolarization map of the heart;

delivering electroporation to the heart via the first electrode, wherein the delivering the electroporation comprises delivering irreversible electroporation or delivering reversible electroporation;

receiving an external signal from a second electrode external to the heart at a second location; and calibrating the external signal with the repolarization signal from the first electrode, wherein the calibrating the external signal comprises measuring a downslope of a t-wave intersection with a baseline.

2. The method of claim 1, wherein the filtering the repolarization signal comprises reducing noise from the repolarization signal.

3. The method of claim 1, wherein the filtering the repolarization signal comprises:

calculating a differential of the repolarization signal; and removing a derivative signal from the repolarization signal.

4. The method of claim 1, wherein the first location and the second location receive signals from a similar area of the heart.

5. The method of claim 1, wherein the calibrating the external signal further comprises moving the external electrode to a third location, and wherein creating the repolarization map of the heart comprises using the external signal to create the repolarization map.

6. The method of claim 1, wherein the calibrating the external signal comprises taking a first order differential of the external signal.

7. The method of claim 1, further comprising receiving an electroporation signal caused by delivering electroporation and detecting a predictable effect of electroporation on the repolarization signal.

8. The method of claim 1, wherein the delivering stimulation further comprises changing a heart rate of the patient via the stimulation, wherein changing the heart rate of the patient causes a change in the repolarization signal of the patient.

9. The method of claim 1, wherein the creating the repolarization map comprises creating the repolarization with magnet-aided navigation and point procurement.

10. The method of claim 1, wherein the creating the repolarization map comprises determining a reference point in the repolarization signal.

11. The method of claim 10, wherein the creating the repolarization map comprises using the reference point to create the repolarization map, wherein the reference point is an end of repolarization.

12. The method of claim 1, further comprising determining variants of the repolarization map from a normal repolarization map.

13. The method of claim 12, wherein the determining variants of the repolarization map comprises comparing the repolarization map with the normal repolarization map and detecting differences between the repolarization map and the normal repolarization map.

14. A method of treating cardiac arrhythmias, the method comprising:

receiving a repolarization signal from a first electrode on a distal portion of a mapping catheter while the distal portion of the mapping catheter is inserted in a heart of a patient such that the first electrode is located at a first location;

filtering the repolarization signal received from the first electrode;

delivering stimulation to the heart via the first electrode, wherein the delivering the stimulation comprises:

delivering a first set of stimulation below a threshold;

increasing a parameter of the first set of stimulation;

detecting a capture is obtained when an intensity of the stimulation crosses the threshold; and creating a repolarization map of the heart.

15. The method of claim 14, wherein the delivering the stimulation further comprises decreasing an intensity of the first set of stimulation and changing an interval between pulses of the first set of stimulation.

* * * * *